US00PP32522P3

(12) United States Plant Patent
Hoogkamp

(10) Patent No.: US PP32,522 P3
(45) Date of Patent: Nov. 24, 2020

(54) ***SPATHIPHYLLUM* PLANT NAMED 'SPAMOCO'**

(50) Latin Name: ***Spathiphyllum* Schott.**
Varietal Denomination: Spamoco

(71) Applicant: Timothy Johan Herman Hoogkamp, Doetinchem (NL)

(72) Inventor: Timothy Johan Herman Hoogkamp, Doetinchem (NL)

(73) Assignee: NUBILUS B.V., Naaldwijk (NL)

( * ) Notice: Subject to any disclaimer, the term of this patent is extended or adjusted under 35 U.S.C. 154(b) by 0 days.

(21) Appl. No.: 16/602,989

(22) Filed: Jan. 11, 2020

(65) Prior Publication Data

US 2020/0229334 P1 Jul. 16, 2020

Related U.S. Application Data

(60) Provisional application No. 62/918,087, filed on Jan. 12, 2019.

(51) Int. Cl.
*A01H 5/02* (2018.01)
*A01H 6/10* (2018.01)
*A01H 6/00* (2018.01)

(52) U.S. Cl.
USPC ..... Plt./364
CPC ..... *A01H 6/00* (2018.05); *A01H 5/02* (2013.01)

(58) Field of Classification Search
USPC ..... Plt./263.1, 364
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Spathiphyllum* plant named 'Spamoco', characterized by its relatively compact, upright, outwardly arching and uniform plant habit; freely clumping growth habit; bushy and dense plants; glossy dark green-colored leaves; freely flowering habit; white-colored spathes that are positioned slightly above to clearly above the foliar plane on strong and erect scapes; and good inflorescence longevity.

3 Drawing Sheets

Figure 1:
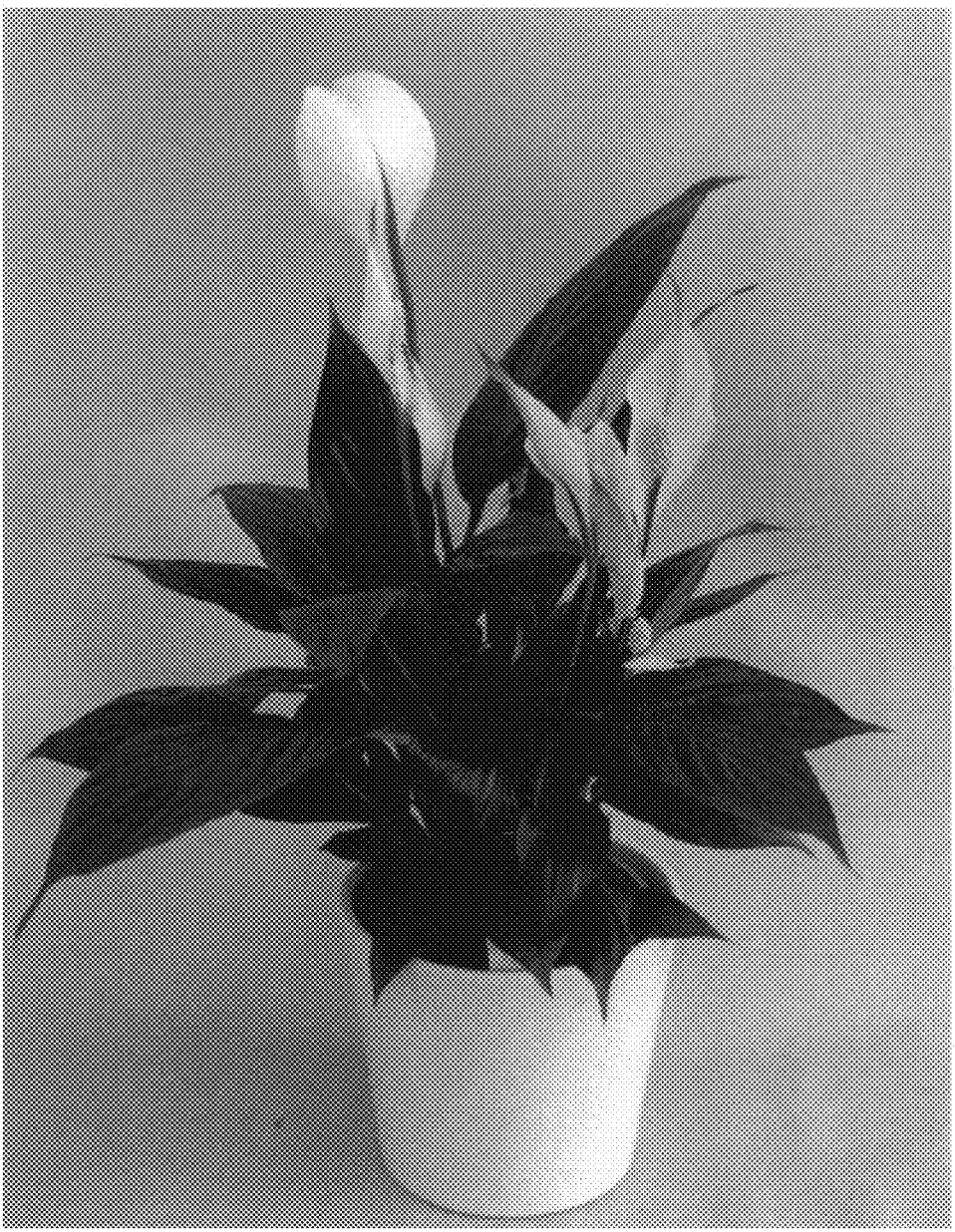

Botanical designation: *Spathiphyllum* Schott.
Cultivar denomination: 'SPAMOCO'.

BACKGROUND OF THE INVENTION

The present invention relates to a new and distinct cultivar of *Spathiphyllum* plant, botanically known as *Spathiphyllum* Schott. and hereinafter referred to by the cultivar name 'Spamoco'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in December, 2012 of a proprietary selection of *Spathiphyllum* Schott. identified as code number 20112154-14, not patented, as the female, or seed, parent with a proprietary selection of *Spathiphyllum* Schott. identified as code number 20120145-01, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in March, 2014.

Asexual reproduction of the new *Spathiphyllum* plant by in vitro meristem culture in a controlled environment in Naaldwijk, The Netherlands since August, 2015 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamoco'. These characteristics in combination distinguish 'Spamoco' as a new and distinct *Spathiphyllum* plant:

1. Relatively compact, upright, outwardly arching and uniform plant habit.
2. Freely clumping growth habit; bushy and dense plants.
3. Glossy dark green-colored leaves.
4. Freely flowering habit.
5. White-colored spathes that are positioned slightly above to clearly above the foliar plane on strong and erect scapes.
6. Good inflorescence longevity.

Plants of the new *Spathiphyllum* differ from plants of the female parent selection in the following characteristics:

1. Plants of the new *Spathiphyllum* are shorter than plants of the female parent selection.
2. Leaves of plants of the new *Spathiphyllum* are darker green in color than leaves of plants of the female parent selection.

Plants of the new *Spathiphyllum* differ from plants of the male parent selection in the following characteristics:

1. Plants of the new *Spathiphyllum* are taller than plants of the male parent selection.
2. Spathes of plants of the new *Spathiphyllum* are white in color whereas spathes of plants of the male parent selection are creamy white in color.

Plants of the new *Spathiphyllum* can also be compared to plants of *Spathiphyllum* Schott. 'Spaamerigro', disclosed in U.S. Plant Pat. No. 31,332. In side-by-side comparisons, plants of the new *Spathiphyllum* differ from plants of 'Spaamerigro' in the following characteristics:

1. Plants of the new *Spathiphyllum* are shorter than plants of 'Spaamerigro'.
2. Leaves of plants of the new *Spathiphyllum* are darker green in color than leaves of plants of 'Spaamerigro'.
3. Scapes of plants of the new *Spathiphyllum* are shorter than scapes of plants of 'Spaamerigro'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet (FIG. 1 of 3) is a side perspective view of a typical plant of 'Spamoco' grown in a container and is the same photograph as filed in the U.S. Provisional Patent application Ser. No. 62/918,087.

Figure 2:
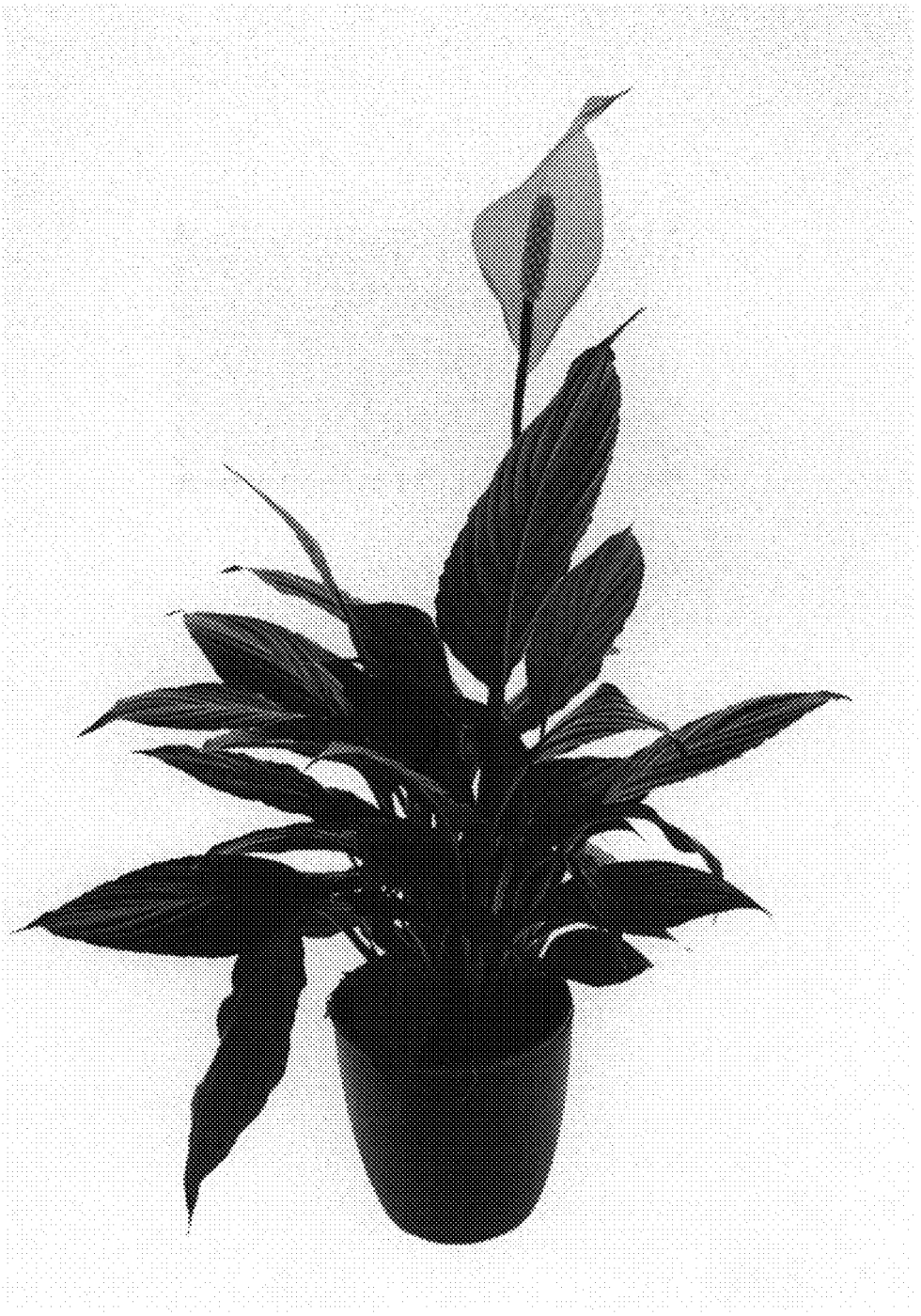

The photograph on the second sheet (FIG. 2 of 3) is a side perspective view of a typical plant of 'Spamoco' grown in a container.

Figure 3:
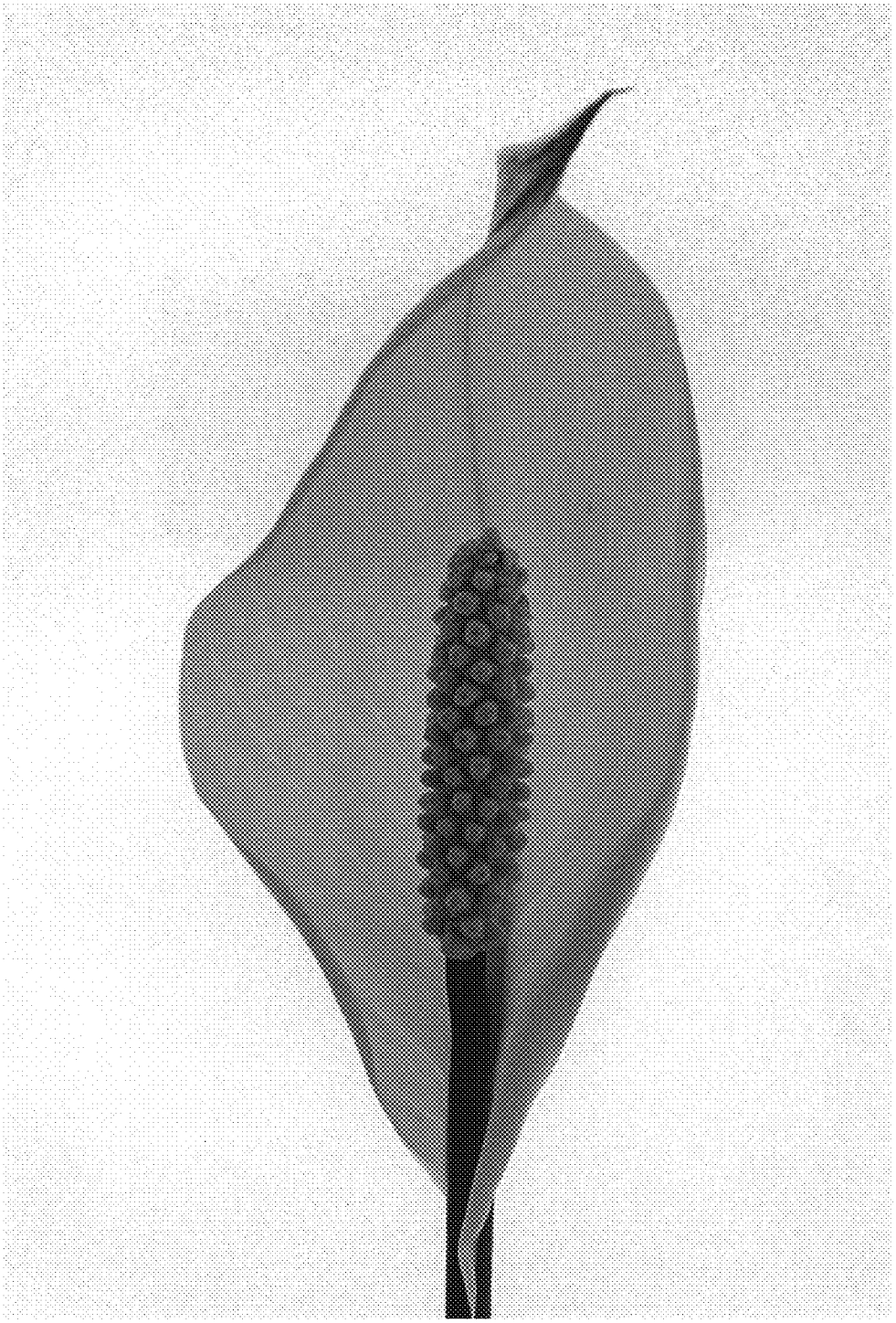

The photograph on the third sheet (FIG. 3 of 3) is a close-up view of a typical inflorescence of 'Spamoco'.

DETAILED BOTANICAL DESCRIPTION

The aforementioned photographs and following observations and measurements describe plants grown during the autumn and winter in 14-cm containers in a glass-covered greenhouse in Naaldwijk, The Netherlands and under cultural practices typical of commercial *Spathiphyllum* production. During the production of the plants, day temperatures ranged from 19° C. to 30° C., night temperatures ranged from 19° C. to 24° C. and light levels averaged 5 klux. Plants were 24 weeks from transplanting rooted young plants when the photographs and the detailed description were taken. In the following description, color references are made to The Royal Horticultural Society Colour Chart, 2015 Edition, except where general terms of ordinary dictionary significance are used.

Botanical classification: *Spathiphyllum* Schott. 'Spamoco'.

Parentage:

*Female, or seed, parent*.—Proprietary selection of *Spathiphyllum* Schott. identified as code number 20112154-14, not patented.

*Male, or pollen, parent*.—Proprietary selection of *Spathiphyllum* Schott. identified as code number 20120145-01, not patented.

Propagation:

*Type*.—By in vitro meristem culture.

*Time to initiate roots, summer*.—About twelve days at temperatures about 23° C.

*Time to initiate roots, winter*.—About 13 days at temperatures about 23° C.

*Time to produce a rooted young plant, summer*.—About 119 days at temperatures about 21° C.

*Time to produce a rooted young plant, winter*.—About 130 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Relatively compact, upright, outwardly arching and uniform plant habit; overall plant shape, broadly inverted triangle; moderately vigorous growth habit and slow to moderate growth rate.

*Clumping habit*.—Freely clumping habit, bushy and dense growth habit with about eleven clumps developing per plant.

*Plant height, from soil level to top of leaf plane*.—About 30.8 cm.

*Plant height, from soil level to top of inflorescences*.—About 49.5 cm.

*Plant diameter or spread*.—About 49.4 cm.

*Leaf description*.—Arrangement: Alternate; simple. Length: About 20.6 cm. Width: About 8.2 cm. Shape: Elliptic. Apex: Long apiculate. Base: Short attenuate. Margin: Entire; moderately undulate; not lobed. Texture and luster, upper and lower surfaces: Smooth, glabrous; glossy. Venation pattern: Pinnate. Color: Developing leaves, upper surface: Darker and more intense than 141A. Developing leaves, lower surface: Close to 137B. Fully expanded leaves, upper surface: Close to between 139A and N189A; venation, close to NN137A to NN137B. Fully expanded leaves, lower surface: Close to NN137C; venation, close to 145A. Petioles: Length (excluding geniculum): About 9.8 cm. Diameter, just below geniculum: About 4 mm. Diameter, at plant base: About 1 cm. Strength: Strong. Texture and luster, upper and lower surfaces: Smooth, glabrous; matte. Color, upper surface: Close to 147D. Color, lower surface: Close to 143A. Geniculum length: About 3 cm. Geniculum diameter: About 4.5 mm. Geniculum texture and luster, upper and lower surfaces: Smooth, glabrous; matte. Geniculum color, upper and lower surfaces: Close to 143B. Wing length: About 10.1 cm. Wing diameter: About 5 mm. Wing color: Close to 137A to 137B.

Inflorescence description:

*Inflorescence arrangement and flowering habit*.—Moderately to strongly cupped erect spathes with columnar spadices held slightly above to clearly above the foliar plane on strong and erect scapes; flowering structures arise from leaf axils; plants begin flowering about five months after transplanting rooted young plants; freely and continuous flowering year-round under greenhouse conditions in The Netherlands; freely flowering habit, typically about six inflorescences developing per plant.

*Fragrance*.—Moderately fragrant; fragrance, sweet and pleasant.

*Inflorescence longevity*.—Inflorescences last more than three weeks on the plant; inflorescences persistent.

*Spathe*.—Length: About 16.3 cm. Width: About 6.8 cm. Depth: About 5 cm. Shape: Elliptic to slightly obovate. Apex: Apiculate; moderate twisting. Base: Attenuate. Margin: Entire; somewhat incurved. Texture and luster, front surface: Smooth, glabrous; somewhat leathery; slightly glossy. Texture and luster, rear surface: Smooth, glabrous; somewhat leathery; moderately glossy. Color: When developing, front surface: Close to 157D; apex, close to 143A. When developing, rear surface: Close to 157C to 157D; apex, close to 143A. Fully developed, front surface: Close to between 155C and 157D; apex, close to 143B; main vein, close to 148D; color does not change with development. Fully developed, rear surface: Close to 155A; apex and main vein, close to 143B; color does not change with development.

*Spadix*.—Length: About 5.2 cm. Diameter: About 1.4 cm. Shape: Columnar; apex, obtuse; base, obtuse; cross-section, circular. Aspect: Close to erect, about 5° from scape axis. Color, immature: Close to 145C. Color, mature: Close to between 155D and 158D. Flowers: Quantity per spadix: Numerous, about 175. Shape: Rounded. Height: About 3 mm. Diameter: About 4 mm. Anther color: Close to NN155B to NN155C. Pollen amount: Scarce. Pollen color: Close to 155B to 155C. Stigma color: Close to between 155D and 158D. Ovary color: Close to 158D.

*Scapes*.—Length: About 39.4 cm. Diameter: About 5 mm. Strength: Strong. Aspect: Erect. Texture and luster: Smooth, glabrous; slightly glossy. Color: Close to 144A.

*Seeds and fruits*.—To date, seed and fruit development have not been observed on plants of the new *Spathiphyllum*.

Pathogen & pest resistance: To date, plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 5° C. to about 40° C. and to be suitable for USDA Hardiness Zones 10 to 13.

It is claimed:

1. A new and distinct *Spathiphyllum* plant named 'Spamoco' as illustrated and described.

* * * * *